United States Patent
Tanaka et al.

(10) Patent No.: US 8,546,483 B2
(45) Date of Patent: Oct. 1, 2013

(54) OIL-IN-WATER ORGANOPOLYSILOXANE EMULSION COMPOSITION, COSMETIC INGREDIENT COMPRISING THIS COMPOSITION, AND METHOD OF PRODUCING A HAIR COSMETIC USING THIS COMPOSITION

(75) Inventors: Hidefumi Tanaka, Chiba (JP); Tsutomu Naganawa, Ichihara (JP)

(73) Assignee: Dow Corning Toray Company, Ltd., Chiyoda-ku, Tokyo (JP)

( * ) Notice: Subject to any disclaimer, the term of this patent is extended or adjusted under 35 U.S.C. 154(b) by 284 days.

(21) Appl. No.: 12/933,069

(22) PCT Filed: Mar. 18, 2009

(86) PCT No.: PCT/JP2009/056033
§ 371 (c)(1),
(2), (4) Date: Nov. 11, 2010

(87) PCT Pub. No.: WO2009/116689
PCT Pub. Date: Sep. 24, 2009

(65) Prior Publication Data
US 2011/0052521 A1  Mar. 3, 2011

(30) Foreign Application Priority Data
Mar. 19, 2008 (JP) ................. 2008-070741

(51) Int. Cl.
*A61Q 5/02* (2006.01)
(52) U.S. Cl.
USPC ........ 524/838; 524/588; 516/55; 424/70.122; 424/70.12

(58) Field of Classification Search
USPC ..................... 524/588, 838; 516/55
See application file for complete search history.

(56) References Cited

U.S. PATENT DOCUMENTS
6,316,545 B1 * 11/2001 Sakuta .......................... 524/837

FOREIGN PATENT DOCUMENTS

| EP | 0798332 A2 | 10/1997 |
|---|---|---|
| EP | 0916690 A1 | 5/1999 |
| EP | 1010717 A2 | 6/2000 |
| JP | 07-188557 A | 7/1995 |
| JP | 11-148011 A | 6/1999 |

OTHER PUBLICATIONS

English language translation and abstract for JP 07-188557 extracted from PAJ database Mar. 22, 2011, 25 pages.
English language translation and abstract for JP 11-148011 extracted from PAJ database Mar. 22, 2011, 33 pages.
PCT International Search Report for PCT/JP2009/056033, dated May 20, 2009, 3 pages.

* cited by examiner

*Primary Examiner* — Margaret Moore
(74) *Attorney, Agent, or Firm* — Howard & Howard Attorneys PLLC

(57) ABSTRACT

To provide a highly storage-stable nonionic oil-in-water organosiloxane emulsion composition that substantially does not contain ionic surfactant and that on a long-term basis does not undergo separation of the emulsion composition. An oil-in-water organosiloxane emulsion composition that characteristically comprises (A) 100 weight parts of organosiloxane, (B) 0.5 to 35 weight parts of organic-modified organosiloxane, (C) 0.5 to 35 weight parts of nonionic surfactant, (D) 0.5 to 15 weight parts of water-soluble solvent, and (E) water, wherein the content of (F) ionic surfactant in the composition is less than 0.1 weight part per 100 weight parts component (A).

12 Claims, No Drawings

OIL-IN-WATER ORGANOPOLYSILOXANE EMULSION COMPOSITION, COSMETIC INGREDIENT COMPRISING THIS COMPOSITION, AND METHOD OF PRODUCING A HAIR COSMETIC USING THIS COMPOSITION

RELATED APPLICATIONS

This application claims priority to and all the advantages of International Patent Application No. PCT/JP2009/056033, filed on Mar. 18, 2009, which claims priority to Japanese Patent Application No. JP 2008-070741, filed on Mar. 19, 2008.

TECHNICAL FIELD

The present invention relates to an oil-in-water organopolysiloxane emulsion composition, a cosmetic ingredient comprising this emulsion composition, and a method of producing a hair cosmetic that characteristically uses this emulsion composition. More particularly, the present invention relates to an oil-in-water organopolysiloxane emulsion composition that exhibits an excellent storage stability and that does not undergo separation on a long-term basis. The present invention further relates to a cosmetic ingredient comprising this emulsion composition, wherein this cosmetic ingredient, because it substantially does not contain an ionic emulsifying agent, can be incorporated regardless of the type of cosmetic base component and exhibits an excellent blending stability. The present invention additionally relates to a method of producing a hair cosmetic that characteristically uses this emulsion composition.

BACKGROUND ART

Oil-in-water organosiloxane emulsion compositions are used in a broad range of fields as an ingredient in, for example, fiber-treatment agents, release agents, cosmetics, polishes, and so forth. Particularly in the case of cosmetic applications, large particle size oil-in-water organosiloxane emulsion compositions have been disclosed based on the expectation of a strong conditioning effect when incorporated into hair cosmetics, for example, shampoos, rinses, and so forth.

For example, Patent Reference 1 (JP 11-148011 A) discloses a cationic emulsion composition that has an average particle size of 1 to 20 microns and that comprises organosiloxane, cationic surfactant, polyhydric alcohol, and water. Patent Reference 2 (JP 07-188557 A) discloses an anionic emulsion composition that has an average particle size of 3 to 100 microns and that comprises organosiloxane, anionic surfactant, and water.

While these emulsion compositions do encompass emulsion compositions that are used as an ingredient in, for example, hair cosmetics, an ionic surfactant is an essential component of these emulsion compositions, and, depending on the ionicity of the base used for the hair cosmetic (e.g., shampoo, rinse, etc.), the stability after the incorporation of such emulsion compositions can be drastically impaired.

Thus, when an anionic emulsion composition is blended into a hair cosmetic base comprising a cationic surfactant, the charge on the surfactant in the base cancels the charge on the surfactant in the emulsion composition and the surfactancy is reduced, which can cause the emulsion in the hair cosmetic to break. In addition, the incorporation of this anionic emulsion composition into a hair cosmetic comprising a cationic surfactant can result in a reduction in the viscosity of the hair cosmetic composition, separation of the constituent components with elapsed time, a decline in the cleaning power of the hair cosmetic, and a timewise deterioration in the tactile sensation. The same is true for the incorporation of a cationic emulsion composition into a hair cosmetic base comprising an anionic surfactant.

Due to this, there has been demand for a hair cosmetic ingredient comprising a nonionic oil-in-water organosiloxane emulsion composition that substantially does not contain ionic emulsifying agent and that may be unproblematically incorporated even into hair cosmetics that have an ionic surfactant—of any ionicity—as their base. There has been particularly strong demand for oil-in-water organosiloxane emulsion composition having a large particle size that substantially does not contain ionic emulsifying agent and that provides an excellent improvement in the tactile sensation of hair cosmetics.

Moreover, within the sphere of the heretofore known nonionic oil-in-water organosiloxane emulsion compositions, a problem in the particular case of the production of large particle size oil-in-water organosiloxane emulsion compositions has been the appearance of separation in such an emulsion composition with elapsed time, and there has been strong demand for improvements in the long-term storage stability sufficient for use as a cosmetic ingredient.

[Patent Reference 1] JP 11-148011 A
[Patent Reference 2] JP 07-188557 A

SUMMARY OF INVENTION

Technical Problems to be Solved

The present inventors carried out concentrated research in order to solve the problems identified above and achieved the present invention as a result. Thus, an object of the present invention is to provide a highly storage-stable nonionic oil-in-water organosiloxane emulsion composition that substantially does not contain ionic surfactant and that on a long-term basis does not undergo separation of the emulsion composition. More particularly, an object of the present invention is to provide a highly storage-stable, large particle size nonionic oil-in-water organosiloxane emulsion composition that has an average particle size for the emulsion particles of 1 to 100 μm as measured by a laser diffraction scattering procedure.

The present invention additionally provides a very suitable application of this nonionic oil-in-water organopolysiloxane emulsion composition as a cosmetic ingredient and particularly as an ingredient of hair cosmetics. The present invention further provides a method of producing a hair cosmetic that uses this nonionic oil-in-water organopolysiloxane emulsion composition.

Solution to Problems

The aforementioned objects are achieved by
"[1] An oil-in-water organopolysiloxane emulsion composition that characteristically comprises
(A) 100 weight parts of organopolysiloxane or organopolysiloxane mixture, that is represented by the general formula $R_a SiO_{(4-a)/2}$ (wherein each R is independently the hydroxyl group or C1-20 monovalent hydrocarbyl that is unsubstituted or that has a portion of its hydrogen atoms replaced by halogen, and $1.8 \leq a \leq 2.2$),
(B) 0.5 to 35 weight parts of organosiloxane that has a viscosity at 25° C. of 10 to 100,000 mPa·s and that characteristically contains in the molecule at least one type of organic group selected from the group consisting of nitrogen atom-containing organic groups and epoxy-functional organic groups,
(C) 0.5 to 35 weight parts of nonionic surfactant,
(D) 0.5 to 15 weight parts of water-soluble solvent, and
(E) 10 to 150 weight parts of water,
wherein the content of (F) ionic surfactant in the composition is less than 0.1 weight part per 100 weight parts component (A).

[1-1] The oil-in-water organopolysiloxane emulsion composition of [1], characterized in that the content of the (F) ionic surfactant is less than 0.01 weight part per 100 weight parts component (A).

[2] The oil-in-water organopolysiloxane emulsion composition according to [1], characterized in that component (B) is organosiloxane that has in its molecule at least one type of monovalent organic group represented by the following structural formulas (1) to (5)

structural formula (1):

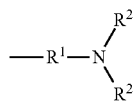

(1)

structural formula (2):

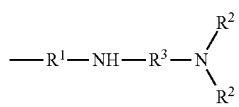

(2)

structural formula (3):

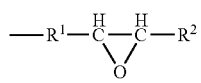

(3)

structural formula (4):

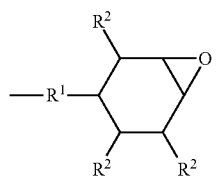

(4)

structural formula (5):

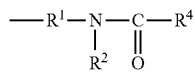

(5)

(in structural formulas (1) to (5),
each $R^1$ is independently C1-20 divalent hydrocarbyl that is unsubstituted or that has a portion of its hydrogen atoms replaced by halogen,
each $R^2$ is independently a monovalent functional group selected from the group consisting of the hydrogen atom, carbinol group, and C1-20 monovalent hydrocarbyl that is unsubstituted or that has a portion of its hydrogen atoms replaced by halogen,
$R^3$ is C1-10 divalent hydrocarbyl that is unsubstituted or that has a portion of its hydrogen atoms replaced by halogen, and
$R^4$ is a monovalent functional group selected from the group consisting of the hydrogen atom, carbinol group, polyoxyalkylene group, and C1-50 monovalent hydrocarbyl that is unsubstituted or that has a portion of its hydrogen atoms replaced by halogen, or is a divalent organic group that is bonded to another hydrocarbon-type compound or to organosiloxane).

[3] The oil-in-water organopolysiloxane emulsion composition according to [2], characterized in that component (B) is organosiloxane that additionally contains in its molecule the straight-chain or branched-chain alkylene represented by structural formula (6) below or the oxyalkylene represented by structural formula (7)

structural formula (6):

    (6)

(q in the formula is a number from 2 to 20)

structural formula (7):

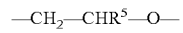    (7)

($R^5$ in the formula is the hydrogen atom or C1-20 monovalent hydrocarbyl that is unsubstituted or that has a portion of its hydrogen atoms replaced by halogen).

[4] The oil-in-water organopolysiloxane emulsion composition according to [1], characterized in that component (D) is an alcohol.

[4-1] The oil-in-water organopolysiloxane emulsion composition according to [4], characterized in that component (D) is at least one alcohol selected from ethanol, propylene glycol, and glycerol.

[5] The oil-in-water organosiloxane emulsion composition according to any of [1] to [4], characterized in that the average particle size of the emulsion particles is in the range of 1 to 100 μm as measured by a laser diffraction•scattering procedure.

[6] The oil-in-water organopolysiloxane emulsion composition according to [1], characterized in that component (A) is chain methylpolysiloxane or cyclic methylpolysiloxane having a viscosity at 25° C. of 0.65 to 30,000,000 mPa·s or is a mixture of these methylpolysiloxanes; component (B) is the straight-chain organosiloxane represented by structural formula (8) given below; component (C) comprises nonionic surfactant; and component (D) is an alcohol structural formula (8):

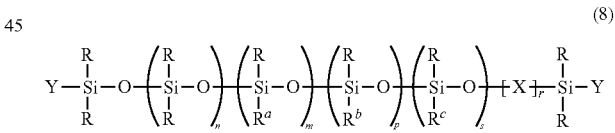

(8)

(in the formula, each R is independently $C_1$-20 monovalent hydrocarbyl that is unsubstituted or that has a portion of its hydrogen atoms replaced by halogen; each $R^a$ is a monovalent organic group independently selected from the group consisting of the monovalent organic groups represented by the preceding structural formulas (1) to (5); $R^b$ is a monovalent functional group selected from the group consisting of the hydroxyl group, carbinol, mercapto, and carboxyl; $R^c$ is a straight-chain or branched-chain alkyl as represented by the following structural formula (6') or is a polyoxyalkylene group as represented by the following structural formula (7'); X is a straight-chain or branched-chain alkylene group as represented by the preceding structural formula (6) or an oxyalkylene group as represented by the preceding structural formula (7); each Y is a group independently selected from R, $R^a$, $R^b$, and $R^c$; (n+m+p+r+s) is a number that provides a viscosity for the organopolysiloxane at 25° C. of 10 to 100, 000 mPa·s; and n, m, p, r, and s are each independently 0 or a positive number, wherein when m=0, a single Y is an organic group represented by $R^a$ or both Y's are organic groups represented by $R^a$)

structural formula (6'):

(6')

(q in the formula is a number from 2 to 20)

structural formula (7'):

structural formula (7'):

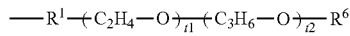

(7')

(in the formula, $R^1$ is C1-20 divalent hydrocarbyl that is unsubstituted or that has a portion of its hydrogen atoms replaced by halogen; $R^6$ is a monovalent functional group selected from the group consisting of the hydrogen atom, carbinol, and C1-20 monovalent hydrocarbyl that is unsubstituted or that has a portion of its hydrogen atoms replaced by halogen; t1 and t2 are each 0 or a positive number; and (t1+t2) is a number in the range of 1 to 50).
[6-1] The oil-in-water organosiloxane emulsion composition according to [6], characterized in that component (C) comprises at least two nonionic surfactants that have different HLB values."

The aforementioned objects are also achieved by
"[7] A cosmetic ingredient comprising the oil-in-water organopolysiloxane emulsion composition according to [1] to [6].
[8] A hair cosmetic ingredient comprising the oil-in-water organopolysiloxane emulsion composition according to [1] to [6].
[9] A method of producing a hair cosmetic, characterized in that the steps for producing the hair cosmetic include a step of:
introducing ionic surfactant and water into a production vessel, thereafter introducing the oil-in-water organopolysiloxane emulsion composition according to [1] to [6] into the production vessel, and mixing using the application of mechanical force."

Advantageous Effects of Invention

The present invention can provide a highly storage-stable nonionic oil-in-water organopolysiloxane emulsion composition that substantially does not contain ionic surfactant and that does not undergo separation of the emulsion composition over a long period of time. More particularly, the present invention can provide a highly storage-stable oil-in-water organosiloxane emulsion composition with nonionic surfactants, having large particle size and that has an average particle size for the emulsion particles of 1 to 100 μm as measured by a laser diffraction•scattering procedure.

Because this emulsion composition substantially does not contain ionic surfactant, it offers the advantages of being blendable into various types of cosmetics—and of providing an excellent storage stability when so blended—without being subject to limitations due to the type of ionic surfactant present in the cosmetic base. As a consequence, the present invention can provide a cosmetic ingredient comprising this emulsion composition, wherein this cosmetic ingredient characteristically exhibits long-term storage stability and an excellent blending stability with various cosmetics. In particular, the present invention can provide a hair cosmetic ingredient comprising this emulsion composition, wherein this hair cosmetic ingredient characteristically exhibits an excellent blending stability with hair cosmetics.

Among the nonionic oil-in-water organopolysiloxane emulsion compositions provided by the present invention, the large particle size emulsion compositions, which have an average particle size for the emulsion particles in the range of 1 to 100 μm as measured by a laser diffraction•scattering procedure, exhibit a very good capacity to adhere to hair. Due to this, these large particle size emulsion compositions are a hair cosmetic ingredient that exhibits an excellent storage stability and an excellent blending stability with hair cosmetics and that is very useful for improving the tactile sensation of hair cosmetics.

In addition, the use of the nonionic oil-in-water organopolysiloxane emulsion composition of the present invention as an ingredient for hair cosmetics makes it possible to provide a method of producing hair cosmetics in which the base is a cleaning agent comprising ionic surfactant.

DESCRIPTION OF EMBODIMENTS

The oil-in-water organopolysiloxane emulsion composition of the present invention will be described in detail first. The oil-in-water organopolysiloxane emulsion composition of the present invention is a nonionic oil-in-water organosiloxane emulsion composition that comprises the components (A) to (E) described below and that is essentially emulsified using nonionic surfactant. A first characteristic feature of the nonionic oil-in-water organosiloxane emulsion composition of the present invention is that it substantially does not contain (F) ionic surfactant. More specifically, the (F) ionic surfactant content in the composition is less than 0.1 weight part per 100 weight parts of the organopolysiloxane designated as component (A), more preferably is less than 0.01 weight part per 100 weight parts component (A), and even more preferably is less than 0.001 weight part per 100 parts component (A). In the most preferred embodiment of the present invention, the emulsion composition does not contain (F) ionic surfactant.

When an oil-in-water organopolysiloxane emulsion composition of the present invention containing (F) ionic surfactant in excess of the limit specified above is used as a cosmetic ingredient, the charge on the surfactant in the emulsion composition cancels the charge on the ionic surfactant used for the cosmetic base, which can result in a lowering of the surface activity and in breaking of the emulsion in the cosmetic. The incorporation of such an emulsion composition into a cosmetic can result in negative effects such as a reduction in the viscosity of the cosmetic composition, a decline in the cleaning power of the cosmetic composition, a timewise deterioration in the tactile sensation, a lack of uniformity in the appearance of the cosmetic composition, and so forth. These tendencies are particularly significant in the case of hair cosmetics, which may contain large amounts of ionic surfactant as a cleaning component.

The (F) ionic surfactant is an anionic surfactant or cationic surfactant, and the oil-in-water organopolysiloxane emulsion composition of the present invention substantially does not contain ionic surfactant as exemplified in the following.

Examples of the anionic surfactant are the salts of saturated higher aliphatic acids and the salts of unsaturated higher aliphatic acids (for example, sodium laurate, sodium stearate, sodium oleate, sodium linolenate, and so forth), the salts of long-chain alkyl sulfates, alkylbenzenesulfonic acids (for example, hexylbenzenesulfonic acid, octylbenzenesulfonic acid, dodecylbenzenesulfonic acid, and so forth) and their salts, polyoxyalkylene alkyl ether sulfate salts, polyoxyalkylene alkenyl ether sulfate salts, the salts of polyoxyethylene alkyl sulfate esters, the salts of the alkyl esters of sulfosuccinic acid, the salts of polyoxyalkylene sulfosuccinic acids, the salts of the alkyl esters of polyoxyalkylene sulfosuccinic acids, alkali metal salts of esters of sulfosuccinic acid with polyoxyalkylene-modified dimethylpolysiloxane, polyoxyalkylene alkylphenyl ether sulfate salts, the salts of long-chain alkanesulfonic acids, long-chain alkylsulfonates, polyoxyethylene alkylphenyl ether sulfate salts, polyoxyalkylene alkyl ether acetate salts, the salts of long-chain alkyl phosphates, the salts of polyoxyalkylene alkyl ether phosphates, acylglutamate salts, α-acylsulfonate salts, long-chain alkylsulfonate salts, alkylarylsulfonate salts, long-chain α-olefinsulfonate salts, alkylnaphthalenesulfonate salts, the salts of long-chain alkanesulfonic acids, long-chain alkyl or alkenyl sulfate salts, long-chain alkylamide sulfate salts, long-chain alkyl or alkenyl phosphate salts, alkylamide phosphate salts, alkyloylalkyltaurate salts, the salts of N-acylamino acids, the salts of sulfosuccinic acid, the salts of alkyl alkyl ether carboxylic acids, the salts of amide ether carboxylic acids, the salts of α-sulfofatty acid esters, alanine derivatives, glycine derivatives, and arginine derivatives. The salts referenced above can be alkali metal salts (e.g., the sodium salt, potassium salt, and so forth), alkanolamine salts (e.g., the triethanolamine salt and so forth), or the ammonium salt.

Examples of the cationic surfactant are alkyltrimethylammonium chloride, stearyltrimethylammonium chloride, lauryltrimethylammonium chloride, cetyltrimethylammonium chloride, beef tallow alkyltrimethylammonium chloride, behenyltrimethylammonium chloride, octyltrimethylammonium hydroxide, dodecyltrimethylammonium hydroxide, stearyltrimethylammonium bromide, behenyltrimethylammonium bromide, distearyldimethylammonium chloride, dicocoyldimethylammonium chloride, dioctyldimethylammonium chloride, di(POE)oleylmethylammonium chloride (2EO), benzalkonium chloride, alkylbenzalkonium chloride, alkyldimethylbenzalkonium chloride, benzethonium chloride, stearyldimethylbenzylammonium chloride, lanolin-derived quaternary ammonium salts, the diethylaminoethylamide of stearic acid, the dimethylaminopropylamide of stearic acid, behenamidopropyldimethylhydroxypropylammonium chloride, stearoylcolaminoformylmethylpyridinium chloride, cetylpyridinium chloride, tall oil alkylbenzylhydroxyethylimidazolinium chloride, and benzylammonium salts.

A second characteristic feature of the oil-in-water organopolysiloxane emulsion composition of the present invention is that it comprises (A) 100 weight parts of an organopolysiloxane represented by the general formula $R_aSiO_{(4-a)/2}$ or a mixture of such organopolysiloxanes (wherein each R is independently the hydroxyl group or C1-20 monovalent hydrocarbyl that is unsubstituted or that has a portion of its hydrogen atoms replaced by halogen, and 1.8≤a≤2.2), (B) 0.5 to 35 weight parts straight-chain or branched-chain organopolysiloxane that has a viscosity at 25° C. of 10 to 10,000 mPa·s and that characteristically contains in the molecule at least one type of organic group selected from the group consisting of nitrogen atom-containing organic groups and epoxy-functional organic groups, (C) 0.5 to 35 weight parts nonionic surfactant, (D) 0.5 to 5 weight parts water-soluble solvent, and (E) 10 to 150 weight parts water and substantially does not contain the (F) ionic surfactant cited above. Components (A) to (E) are described in detail in the following.

Component (A) is the base component of the nonionic oil-in-water organosiloxane emulsion composition of the present invention and is organopolysiloxane represented by the general formula $R_aSiO_{(4-a)/2}$ or is a mixture of such organopolysiloxanes.

Each R in this formula is independently the hydroxyl group or C1-20 monovalent hydrocarbyl that is unsubstituted or has a portion of its hydrogen atoms replaced by halogen, and 1.8≤a≤2.2 in the formula. R is specifically exemplified by saturated aliphatic hydrocarbyl comprising C1-20 alkyl, for example, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, and nonadecyl; unsaturated aliphatic hydrocarbyl comprising C1-20 alkenyl, for example, vinyl, propenyl, and hexenyl; saturated alicyclic hydrocarbyl such as cyclopentyl and cyclohexyl; aromatic hydrocarbyl such as phenyl, tolyl, and naphthyl; and fluorinated hydrocarbyl, such as fluoroalkyl, as yielded by replacing a portion of the hydrogen atoms in the hydrocarbyl cited above with halogen, for example, fluorine. Methyl is preferably at least 70 mol % of all the R and more preferably is at least 90 mol % of R.

The organopolysiloxane that is component (A) preferably has a viscosity at 25° C. of 0.65 to 30,000,000 mPa·s, and any of the following structures can be used for the molecular structure of this organopolysiloxane: cyclic, straight chain, branched chain, and resinous.

The organopolysiloxane that is component (A) may be a single organopolysiloxane or may be an organopolysiloxane mixture comprising two or more organopolysiloxanes, and any mixing ratio can be used in the latter case.

This organopolysiloxane can be specifically exemplified by the following, in each case with a viscosity of 0.65 to 30,000,000 mPa·s at 25° C.: chain methylpolysiloxanes such as dimethylpolysiloxanes, methylphenylpolysiloxanes, α,ω-dihydroxydimethylpolysiloxanes, and so forth, and cyclic methylpolysiloxanes such as octamethylcyclotetrasiloxane, decamethylcyclopentasiloxane, dodecamethylcyclohexasiloxane, and so forth. The present invention can use a single one of these organopolysiloxanes or can use a mixture in which a plurality of these organopolysiloxanes have been combined.

When component (A) is a mixture of organopolysiloxanes, a preferred component (A) is a mixture of at least two chain methylpolysiloxanes that have different viscosities or a mixture of a chain methylpolysiloxane having a relatively high degree of polymerization (DP) with a cyclic methylpolysiloxane such as octamethylcyclotetrasiloxane. Particularly when the nonionic oil-in-water organosiloxane emulsion composition according to the present invention is used as an ingredient for hair cosmetics, component (A) is preferably an organopolysiloxane mixture that contains at least one relatively high DP chain methylpolysiloxane that has a viscosity at 25° C. in the range of 3,000 to 30,000,000 mPa·s. The use of such a high DP chain methylpolysiloxane can be expected to provide an additional increment in the improvement in the hair cosmetic use sensation that is generated by the incorporation of the emulsion composition.

More specifically, the following is a preferred component (A) when component (A) is a mixture of organopolysiloxanes: a mixture, in a weight ratio of 1:99 to 99:1, of a component (A-1) comprising chain methylpolysiloxane having a viscosity at 25° C. of 3,000 to 30,000,000 mPa·s and a component (A-2) comprising chain methylpolysiloxane having a viscosity in the range of 0.65 to 5,000 mPa·s at 25° C. that is lower than that of component (A-1). An even more preferred implementation of the component (A) of the present invention is a mixture, in a weight ratio of 5:95 to 90:10, of chain methylpolysiloxane having a viscosity at 25° C. of 5,000 to 30,000,000 mPa·s as the aforementioned component (A-1) and chain methylpolysiloxane having a viscosity at 25° C. of 0.65 to 3,000 mPa·s as the aforementioned component (A-2).

The following is also a preferred component (A) when component (A) is a mixture of organopolysiloxanes: a mixture, in a weight ratio of 1:99 to 99:1, of chain methylpolysiloxane having a viscosity at 25° C. in the range of 3,000 to 10,000,000 mPa·s and at least one cyclic methylpolysiloxane selected from the group consisting of octamethylcyclotetrasiloxane, decamethylcyclopentasiloxane, and dodecamethylcyclohexasiloxane, wherein a mixture having a mixing ratio of 5:95 to 90:10 is particularly preferred.

Component (B) is an organic-modified siloxane that has a specific functional group and is a component that, by its use in combination with the nonionic surfactant comprising component (C) and the water-soluble solvent comprising component (D), inhibits separation of the nonionic oil-in-water organosiloxane emulsion composition of the present invention and provides a substantially improved storage stability. Component (B) must be added to the emulsion composition of the present invention at from 0.5 to 35 weight parts per 100 weight parts component (A) and is preferably added at from 1.0 to 25 weight parts per 100 weight parts component (A) and is more preferably added at from 1.5 to 20 weight parts per 100 weight parts component (A).

When the component (B) content is below the lower limit cited above, the nonionic oil-in-water organosiloxane emulsion composition exhibits an unsatisfactory storage stability and separation can occur quickly (using a storage period of from several days to about 4 weeks as the yardstick). When, on the other hand, the component (B) content exceeds the upper limit cited above, the nonionic oil-in-water organosiloxane emulsion composition assumes an excessively high viscosity, which can make handling problematic; in addition, the storage stability of the emulsion composition becomes unsatisfactory and separation can occur quickly.

The organic-modified siloxane comprising component (B) is organosiloxane that has a viscosity at 25° C. of 10 to 100,000 mPa·s and that characteristically contains in the molecule at least one type of organic group selected from the group consisting of nitrogen atom-containing organic groups and epoxy-functional organic groups.

The nitrogen atom-containing organic group encompassed by component (B) can be specifically exemplified by the amino group represented by the following structural formula (1), the diamino group represented by the following structural formula (2), and the amide bond-containing organic group represented by the following structural formula (5).

structural formula (1):

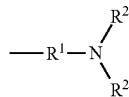

(1)

structural formula (2):

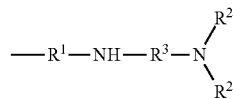

(2)

structural formula (5):

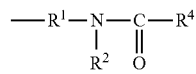

(5)

Each $R^1$ in the preceding structural formulas (1), (2), and (5) is independently C1-20 divalent hydrocarbyl that is unsubstituted or has a portion of its hydrogen atoms replaced by halogen, C2-10 straight-chain or branched-chain alkylene, fluoroalkylene, or arylene. Examples of $R^1$ preferred for the present invention are ethylene, propylene, and butylene.

Each $R^2$ is a monovalent functional group independently selected from the group consisting of the hydrogen atom, the carbinol group, and C1-20 monovalent hydrocarbyl that is unsubstituted or has a portion of its hydrogen atoms replaced by halogen, and can be exemplified by the hydrogen atom, straight-chain and branched-chain C1-10 alkyl, fluoroalkyl, aralkyl, and aryl. Examples of $R^2$ preferred for the present invention are the hydrogen atom, methyl, ethyl, propyl, phenyl, and benzyl.

$R^3$ is C1-10 divalent hydrocarbyl that is unsubstituted or has a portion of its hydrogen atoms replaced by halogen and can be exemplified by straight-chain and branched-chain C1-5 alkylene. Examples of $R^3$ preferred for the present invention are methylene, ethylene, propylene, and butylene.

$R^4$ is a monovalent functional group selected from the group consisting of the hydrogen atom, carbinol group, polyoxyalkylene groups, and C1-50 monovalent hydrocarbyl that is unsubstituted or has a portion of its hydrogen atoms replaced by halogen, or is a divalent organic group that is bonded to another hydrocarbon compound or organosiloxane. $R^4$ can be exemplified by the hydrogen atom, straight-chain and branched-chain C1-20 alkyl, fluoroalkyl, aralkyl, and aryl. The divalent organic group that is bonded to another hydrocarbon compound or organosiloxane can be exemplified by C2-10 straight-chain and branched-chain alkylene, fluoroalkylene, and arylene. The amide bond-containing organic group represented by structural formula (5) in the present invention is preferably a group modified by an aliphatic acid amide or a group modified by an aliphatic acid polyether amide. Preferred examples of $R^4$ are the hydrogen atom, straight-chain and branched-chain C1-50 alkyl, fluoroalkyl, aralkyl, aryl, and polyoxyalkylene.

The epoxy-functional organic group encompassed by component (B) can be specifically exemplified by the epoxy-modified group represented by the following structural formula (3) and the alicyclic-type epoxy-modified group represented by the following structural formula (4).

structural formula (3):

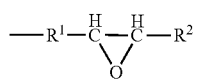 (3)

structural formula (4):

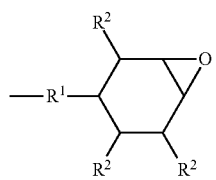 (4)

$R^1$ and $R^2$ in the preceding structural formulas (3) and (4) are the same groups as described above, wherein the hydrogen atom is particularly preferred for $R^2$.

Component (B) in the present invention is organosiloxane that contains in the molecule at least one type of organic group selected from the group consisting of nitrogen atom-containing organic groups and epoxy-functional organic groups as described above, and preferably also contains in the molecule the straight-chain or branched-chain alkylene group represented by the following structural formula (6) or the oxyalkylene group represented by the following structural formula (7). These divalent organic groups may be bonded in main chain position in the component (B) molecule, in side chain position in the component (B) molecule, or in molecular chain terminal position in the component (B) molecule.

structural formula (6):

—$C_qH_{2q}$— (6)

structural formula (7):

—$CH_2$—$CHR^5$—O— (7)

The subscript q in structural formula (6) is a number from 2 to 20, and specific examples here are C3-20 straight-chain and branched-chain alkylene groups. In addition, when the organic group represented by structural formula (6) is bonded in side chain position or molecular chain terminal position in the component (B) molecule, C2-20 straight-chain and branched-chain alkyl with structural formula (6') is a preferred example of the organic group participating in such bonding. In those instances in which the organosiloxane emulsion composition of the present invention is incorporated into a cosmetic that contains large amounts of a hydrocarbon-type oil such as paraffin, a component (B) that contains C8-20 long-chain alkyl in the molecule is preferably used in order to improve the affinity with the hydrocarbon-type oil.

structural formula (6'):

—$C_qH_{2q+1}$ (6')

(q in the formula is a number from 3 to 20)

$R^5$ in structural formula (7) is the hydrogen atom or C1-20 monovalent hydrocarbyl that is unsubstituted or has a portion of its hydrogen atoms replaced with halogen; examples of $R^5$ are the hydrogen atom, methyl, ethyl, propyl, and phenyl. The hydrogen atom and methyl are preferred examples of $R^5$.

The oxyalkylene group represented by structural formula (7) may be a structure in which from 1 to 50 are bonded. Thus, a component (B) suitable for use in the present invention is organosiloxane that has in the molecule a polyoxyalkylene linkage that contains the oxyethylene unit ($C_2H_4O$) or the oxypropylene unit ($C_3H_6O$).

For those instances in which the organic group represented by structural formula (7) is bonded in side chain position or molecular chain terminal position in the component (B) molecule, the polyoxyalkylene group represented by structural formula (7') is an example of the organic group participating in such bonding.

structural formula (7'):

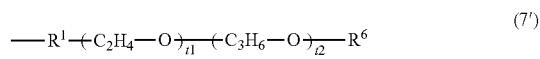 (7')

$R^1$ in structural formula (7') is the same as previously defined. $R^6$ is a monovalent functional group selected from the group consisting of the hydrogen atom, carbinol group, and C1-20 monovalent hydrocarbyl that is unsubstituted or has a portion of its hydrogen atoms replaced by halogen, and is exemplified in the present invention by the hydrogen atom, methyl, ethyl, and hydroxyethyl. t1 and t2 are each zero or a positive number and (t1+t2) is a number in the range from 1 to 50. (t1+t2) is particularly preferably a number in the range from 2 to 40.

As its other functional group or groups ($R^b$), the above-described component (B) may contain a monovalent functional group selected from the group consisting of the hydroxyl group, carbinol groups such as hydroxyethyl, the mercapto group, and the carboxyl group. Moreover, and insofar as the objects of the present invention are not impaired, component (B) may be an organic-modified organosiloxane that contains in the molecule an organic group not corresponding to structural formulas (1) to (7), (6'), and (7'), for example, a silicone chain structure that has a siloxane dendrimer structure, a sugar chain-modified group, and so forth.

The straight-chain organosiloxane represented by the following structural formula (8) is an example of the organosiloxane comprising the component (B) under consideration.

structural formula (8):

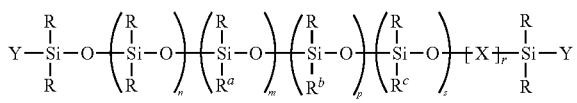 (8)

Each R in structural formula (8) is independently C1-20 monovalent hydrocarbyl that is unsubstituted or has a portion of its hydrogen atoms replaced by halogen, and can be exemplified by saturated aliphatic hydrocarbyl comprising C1-20 alkyl, for example, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, and nonadecyl; unsaturated aliphatic hydrocarbyl comprising C1-20 alkenyl, for example, vinyl, propenyl, and hexenyl; saturated alicyclic hydrocarbyl such as cyclopentyl and cyclohexyl; aromatic hydrocarbyl such as phenyl, tolyl, and naphthyl; and fluorinated hydrocarbyl, such as fluoroalkyl, as yielded by replacing a portion of the hydrogen atoms in the hydrocarbyl cited above with halogen, for example, fluorine. With regard to the R under consideration, methyl is preferably at least 70 mol % of all the R and more preferably is at least 90 mol % of R.

Each $R^a$ in the formula is independently a monovalent organic group selected from the group consisting of the monovalent organic groups represented by structural formulas (1) to (5) provided above; moreover, when m=0, the organic group Y is $R^a$ at one terminal or at both terminals of the organosiloxane represented by structural formula (8). Thus, the organosiloxane represented by structural formula (8) contains in its molecule at least one monovalent organic group selected from the group consisting of the monovalent organic groups represented by structural formulas (1) to (5).

$R^b$ is a monovalent functional group selected from the group consisting of the hydroxyl group, carbinol group, mercapto group, and carboxyl group, while $R^c$ is the straight-chain or branched-chain alkyl represented by the preceding structural formula (6') or is the polyoxyalkylene group represented by the preceding structural formula (7'). Rc in component (B) of the present invention is preferably a polyoxyalkylene group comprising the polyoxyethylene group, polyoxypropylene group, or both of these units.

X is the straight-chain or branched-chain alkylene group represented by the preceding structural formula (6) or is the oxyalkylene group represented by the preceding structural formula (7), and a molecular chain may be formed in which X or a linking functional group comprising X is bonded in the molecule in alternation with siloxane units. Y is a group selected from R, $R^a$, $R^b$, and $R^c$. When m=0, however, one Y is $R^a$ or both Y's are $R^a$.

The value of (n+m+p+r+s) is a number that provides a viscosity for the organopolysiloxane at 25° C. of 10 to 100,000 mPa·s, and n, m, p, r, and s are each independently 0 or a positive number. (n+m) is preferably a number in the range from 50 to 1,000. (n+m+p+r+s) in component (B) of the present invention is preferably a number that provides a viscosity for the organopolysiloxane at 25° C. in the range of 100 to 75,000 mPa·s and more preferably is a number that provides a range of 300 to 50,000 mPa·s.

A particularly preferred component (B) of the present invention contains, in addition to the at least one Ra present in its molecule, at least one polyoxyalkylene group comprising the polyoxyethylene group or polyoxypropylene group, in a region selected from the terminals (—Y), side chains (—$R^c$), and main chain (—Xr—) of the molecular chain. In other words, preferably either r or s is a positive number or when r=0 and s=0 at least one Y is the polyoxyalkylene group.

Optimal examples of the component (B) under consideration are organic-modified polysiloxanes that have a viscosity at 25° C. in the range from 100 to 50,000 mPa·s and that are selected from the group consisting of amino-modified siloxanes, epoxy-modified siloxanes, aliphatic amide-modified siloxanes, aminopolyether-modified siloxanes, amidepolyether-modified siloxanes, and epoxypolyether-modified siloxanes. A single one of these organic-modified siloxanes (=component (B)) may be used or a plurality may be used in combination.

Component (C) is nonionic surfactant and is the main surfactant in the oil-in-water organosiloxane emulsion according to the present invention. Through the use of component (C) in combination with the previously described component (B) and the component (D) described below, an emulsified dispersion that exhibits long-term stability is formed substantially without using ionic surfactant.

Component (C) must be added to the emulsion composition of the present invention in the range from 0.5 to 35 weight parts per 100 weight parts component (A) and is preferably added at from 1.0 to 25 weight parts per 100 weight parts component (A) and more preferably is added at from 1.5 to 20 weight parts per 100 weight parts component (A).

When the amount of component (C) incorporation is below the above-cited lower limit, the nonionic oil-in-water organosiloxane emulsion composition exhibits an unsatisfactory storage stability and separation can occur quickly (using a storage period of from several days to about 4 weeks as the yardstick). When, on the other hand, the amount of component (C) incorporation exceeds the above-cited upper limit, the viscosity of the nonionic oil-in-water organosiloxane emulsion composition is excessively high and handling can become problematic; in addition, the emulsion composition evidences an unsatisfactory storage stability and separation can occur quickly.

The component (C) used in the present invention can be exemplified by the following: ethylene glycol/aliphatic acid esters, polyethylene glycol/aliphatic acid esters, propylene glycol/aliphatic acid esters, polypropylene glycol/aliphatic acid esters, glycol/aliphatic acid esters, trimethylolpropane/aliphatic acid esters, pentaerythritol/aliphatic acid esters, glucoside derivatives, the aliphatic acid esters of glycerol alkyl ethers, trimethylolpropaneoxyethylene alkyl ethers, aliphatic acid amides, alkylolamides, alkylamine oxides, lanolin and its derivatives, castor oil derivatives, hardened castor oil derivatives, sterols and their derivatives, polyoxyethylene alkyl ethers, polyoxyethylene alkylaryl ethers, polyoxyethylene alkylamines, polyoxyethylene aliphatic acid amides, polyoxyethylene alkylolamides, polyoxyethylene diethanolamine/aliphatic acid esters, polyoxyethylene trimethylolpropane/aliphatic acid esters, polyoxyethylene alkyl ether/aliphatic acid esters, polyoxyethylene-polyoxypropylene glycols, polyoxyethylene-polyoxypropylene alkyl ethers, polyoxyethylene-polyoxypropylene polyhydric alcohol ethers, glycerol/aliphatic acid esters, polyglycerol/aliphatic acid esters, polyoxyethylene glycerol/aliphatic acid esters, sorbitan/aliphatic acid esters, polyoxyethylene sorbitan/aliphatic acid esters, sucrose/aliphatic acid esters, methyl(polyoxyethylene)siloxane•dimethylsiloxane copolymers, and methyl(polyoxypropylene)siloxane•dimethylsiloxane copolymers. A single one of these compounds may be used in the present invention or a combination of a plurality of these compounds may be used.

The use in the emulsion composition of the present invention of at least two types of nonionic surfactants having different HLB value is particularly preferred from the standpoint of the emulsion stability of the large particle size emulsion compositions and from the standpoint of emulsion composition storage stability. Based on the HLB value (hydrophilic-lipophilic balance value) referenced by the present invention on the HLB as defined by the Griffin method, the co-use is preferred, in a weight ratio of 0.5:9.5 to 9.5:0.5, of at least one nonionic surfactant that has an HLB in the range of 4.0 to 11.0 and at least one nonionic surfactant that has an HLB in the range of 11.1 to 20.0. An optimal weight ratio between or among the at least two nonionic surfactants having different HLB values can be selected as appropriate considering the particle size of the emulsion composition and the type and concentration of component (A).

Component (D) is a water-soluble solvent and is a hydrophilic compound that contains in its molecule a structure such as the hydroxyl group, an ether linkage, and so forth. The use of this component (D) in combination with the previously described components (B) and (C) enables an emulsified dispersion that exhibits long-term stability to be formed substantially without using ionic surfactant.

Component (D) must be added to the emulsion composition of the present invention at from 0.5 to 15 weight parts per 100 weight parts component (A) and preferably is added at from 0.75 to 10 weight parts per 100 weight parts component (A) and more preferably is added at from 1.0 to 5.0 weight parts per 100 weight parts component (A).

When the amount of component (D) incorporation is below the above-cited lower limit, the nonionic oil-in-water organosiloxane emulsion composition exhibits an unsatisfactory storage stability and separation can occur quickly (using a storage period of from several days to about 4 weeks as the yardstick). When, on the other hand, the amount of component (D) incorporation exceeds the above-cited upper limit, the viscosity of the nonionic oil-in-water organosiloxane emulsion composition is excessively high and handling can become problematic; in addition, the emulsion composition evidences an unsatisfactory storage stability and separation can occur after a short storage time.

Alcohols and ethers are examples of the component (D) used in the present invention, wherein alcohols are particularly preferred and C1-20 aliphatic alcohols and polyhydric alcohols are very suitably used. The following are specific examples of component (D): ethanol, n-propanol, isopropyl alcohol, eicosane glycol, ethylene glycol, butyl diglycol, octacosane glycol, octadecane glycol, glycerol, polyethylene glycol, diethylene glycol, diglycerol, dipropylene glycol, tetracosane glycol, tetramethyltrihydroxyhexadecane, docosane glycol, triethylene glycol, 1,3-butylene glycol, propylene glycol, hexacosane glycol, hexadecane glycol, hexylene glycol, ethylene glycol monomethyl ether, ethylene glycol monobutyl ether, trimethylolpropane, pentaerythritol, sorbitol, and so forth. At least one alcohol selected from the group consisting of ethanol, dipropylene glycol, and glycerol is most preferably used as component (D). A single one of the preceding compounds may be used in the present invention or the combination of a plurality of the preceding compounds may be used.

Component (E) is water and is the dispersion medium for the emulsion composition according to the present invention. This water should not contain a component harmful to the human body and is preferably pure and can be exemplified by tap water, purified water, and mineral water.

The emulsion composition of the present invention must contain component (E) at from 10 to 150 weight parts per 100 weight parts component (A) and preferably contains component (E) at from 20 to 100 weight parts per 100 weight parts component (A) and more preferably contains component (E) at from 30 to 70 weight parts per 100 weight parts component (A). The addition of the water (=component (E)) in the aforementioned range is critical for the realization of storage stability by the emulsion composition, which is one of the effects of the present invention.

When the amount of component (E) incorporation is below the above-cited lower limit, the viscosity of the nonionic oil-in-water organosiloxane emulsion composition is excessively high and handling can become problematic; in addition, the emulsion composition evidences an unsatisfactory storage stability and separation can occur quickly. When the amount of component (E) incorporation exceeds the above-cited upper limit, the nonionic oil-in-water organosiloxane emulsion composition—and particularly the large particle size emulsion composition—exhibits an unsatisfactory storage stability notwithstanding the fact that it is an emulsion system obtained using the combination of the components (A) to (D) described above and separation can occur quickly (using a storage period of from several days to about 4 weeks as the yardstick).

The oil-in-water organosiloxane emulsion composition of the present invention characteristically comprises the components (A) to (E) described above and characteristically substantially does not contain (F) ionic surfactant. However, the oil-in-water organosiloxane emulsion composition of the present invention may incorporate, within a range in which the objects of the present invention are not impaired, other additives known as additives for organosiloxane emulsions; these other additives may be incorporated for various purposes, for example, to provide additional improvements in the blending stability when the obtained organosiloxane emulsion composition is blended into, for example, another composition, to prevent biocontamination due to the growth of, for example, microorganisms, after the emulsion has been prepared, and to prevent transport container corrosion.

These other additives can be exemplified by pH modifiers, preservatives, antimolds, antirust agents, thickeners, melting point depressants, freeze/thaw stabilizers, oxidation inhibitors, chelating agents, fragrances, pigments, and colorants. A single one of these components may be added in the present invention or the combination of a plurality of these components may be added. Particularly in those instances in which the oil-in-water organosiloxane emulsion composition of the present invention is employed as a cosmetic ingredient, the addition of a pH modifier, preservative, antimold, and/or antirust agent is particularly preferred.

These other additives preferably are dissolved or dispersed in a portion of the water (component (E)) to prepare a uniform aqueous solution or dispersion, which is then mixed with the other components. The quantity of use for these other additives varies as a function of the type of additive and the purpose of its addition, but in general is less than 10 weight parts per 100 weight parts component (A)

The emulsion particle size of the oil-in-water organosiloxane emulsion composition of the present invention can be designed and selected as appropriate in view of the emulsifying means, infra, and the quantity of addition of the aforementioned components (A) to (E). In those instances in which the emulsion composition of the present invention is used as a cosmetic ingredient and particularly in those instances where it is used as an ingredient for a hair cosmetic, the average particle size of the emulsion particles as measured by a laser diffraction•scattering procedure (referred to hereafter simply as the "average emulsion particle size") is preferably in the range from 1 to 100 µm, more preferably in the range from 1 to 20 µm, and most preferably in the range from 1.5 to 10 µm. The incorporation of this large particle size oil-in-water organosiloxane emulsion composition in a hair cosmetic accrues the advantage of improving the capacity of the organosiloxane to remain on the hair when the hair cosmetic is rinsed out and thereby enabling the realization of an excellent conditioning effect, i.e., imparting luster and a smooth, resilient, and elastic feel to the hair, improving hair comb through, and so forth.

The oil-in-water organosiloxane emulsion composition of the present invention again exhibits an excellent long-term storage stability even when implemented as described above substantially without the use of (F) ionic surfactant as a large particle size oil-in-water organosiloxane emulsion composition having an average emulsion particle size in the range of 1 to 100 µm.

The oil-in-water organosiloxane emulsion composition of the present invention can be produced by emulsifying the aforementioned components (A) to (E) plus any optional other additives by the application of mechanical force using one or two or more of the known stirring devices, mixing devices, and/or emulsifying devices, e.g., a paddle blade-equipped stirrer, propeller stirrer, Henschel-type stirrer, TK Homo Mixer (Tokushu Kika Kogyo Co., Ltd.), TK Homo Disper (Tokushu Kika Kogyo Co., Ltd.), high-pressure emulsifying device, colloid mill, or vacuum emulsifying device.

In an example of a method for producing the emulsion composition of the present invention, components (A) to a portion of component (E) are preliminarily mixed in a production container using a stirred mixing device such as a paddle blade-equipped stirrer; this mixture is thereafter emulsified using a high-shear emulsifying device such as a high-pressure emulsifying device, a colloid mill, or a colloid mixer; and the remainder of component (E) and the other additives are introduced with stirring and mixing. The present invention, however, is not limited to this production method.

The oil-in-water organopolysiloxane emulsion composition of the present invention is well adapted for use as a cosmetic ingredient. Nor is there a particular limitation on the type of cosmetic into which the oil-in-water organosiloxane emulsion composition of the present invention can be incorporated, and applicable cosmetics can be exemplified by skin cosmetics such as skin cleansers, skin care cosmetics, make-up cosmetics, antiperspirants, UV protectants, and so forth; hair cosmetics such as hair cleansers, hairdressing products, hair colorants, hair tonics and hair growth agents, hair rinses, and so forth; bath cosmetics; perfumes and colognes; and so forth. Incorporation into hair cosmetics is particularly preferred.

Hair cosmetics as described above can be prepared by introducing water and the ionic surfactant that will form the hair cosmetic base into a production container; thereafter introducing the oil-in-water organosiloxane emulsion composition according to the present invention into the production container; and mixing by the application of mechanical force.

The use of the oil-in-water organosiloxane emulsion composition of the present invention supports and enables the facile incorporation of emulsion particles comprising a desired organosiloxane even into a hair cosmetic that has an ionic surfactant (i.e., either a cationic surfactant or an anionic surfactant) as its base and yields the advantage of a substantial improvement in the blending stability by organosiloxane in hair cosmetics. Even in the case of large particle size organosiloxane emulsions, long-term storage stability can be obtained and a satisfactory storage interval—from production of the emulsion composition up to its use by actual incorporation into a cosmetic—can be secured. This creates a benefit to commercial cosmetic production processes in that a step for returning the emulsion composition to a uniform condition, e.g., stirring and mixing, is no longer required.

Because the oil-in-water organopolysiloxane emulsion composition according to the present invention exhibits an excellent blending stability for cosmetics, once a cosmetic has been produced, and particularly once a hair cosmetic has been produced, the cosmetic exhibits an excellent timewise stability and does not undergo timewise changes in appearance (e.g., a decline in viscosity, separation, and so forth) or cause nozzle clogging. As a consequence, long-term stable storage is made possible even when the cosmetic is filled in, for example, a transparent container and the cosmetic can be displayed and sold as a product that exhibits an excellent use sensation and an excellent appearance.

EXAMPLES

Examples and comparative examples are provided below in order to specifically describe the present invention; however, the present invention is not limited by the examples that follow. Parts denote weight parts in the examples and comparative examples. The viscosity in the examples and comparative examples refers to the viscosity measured at 25° C. using a rotary viscometer. The following methods were used to evaluate the oil-in-water organosiloxane emulsion compositions that were produced.

[Emulsion Composition Storage Stability]

The produced organosiloxane emulsion composition was weighed into a 200-cc glass bottle and was held at quiescence at room temperature. The state of the emulsion composition was visually monitored, and the time (weeks) until the occurrence of separation in the emulsion was measured.

[Particle Size of the Emulsion Particles]

The average particle size was determined from the median size (50% cumulative average particle size) yielded by measurement of the average emulsion particle size of the produced organosiloxane emulsion composition using a laser diffraction/scattering instrument for particle distribution measurement (LA-750 from HORIBA, Ltd.).

[Stability of Blending into an Ionic Cosmetic Base]

An ionic cosmetic base was prepared using ionic surfactant and the methods described below (Production Examples 3 and 4). 97.0 weight parts of this ionic cosmetic base and 3.0 weight parts of the organosiloxane emulsion composition were introduced into a container and were stirred/mixed until the entire mass reached uniformity. The status of the mixed composition after standing for one day was checked visually to determine the presence/absence of changes in the appearance, for example, separation of the oil phase and so forth.

Example 1

100.0 parts of (A) dimethylpolysiloxane (viscosity of approximately 5,000 mPa·s), 8.3 parts of (B) amino-modified dimethylpolysiloxane (viscosity of approximately 1,200 mPa·s, amino group content of approximately 0.9%) represented by the following structural formula (P-1), 2.8 parts of (C-1) polyoxyethylene (4) lauryl ether (HLB=9.7), 8.0 parts of (C-2) polyoxyethylene (23) lauryl ether (HLB=16.9), 2.5 parts of (D) ethanol, and 44.7 parts of (E) purified water were weighed into a container and were stirred•mixed to uniformity. This was followed by emulsification of the resulting mixture using a colloid mill and the addition of 0.3 part of 80% acetic acid to yield emulsion composition (1).

structural formula:

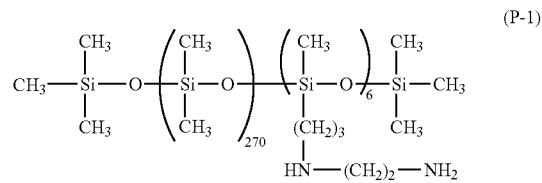

Example 2

100.0 parts of (A) dimethylpolysiloxane (viscosity of approximately 5,000 mPa·s), 8.3 parts of (B) amino-modified dimethylpolysiloxane (viscosity of approximately 1,200 mPa·s, amino group content of approximately 0.9%) represented by the preceding structural formula (P-1), 2.8 parts of (C-1) polyoxyethylene (4) lauryl ether (HLB=9.7), 8.0 parts of (C-2) polyoxyethylene (23) lauryl ether (HLB=16.9), 2.5 parts of (D) glycerol, and 44.7 parts of (E) purified water were weighed into a container and were stirred•mixed to uniformity. This was followed by emulsification of the resulting mixture using a colloid mill and the addition of 0.3 part of 80% acetic acid to yield emulsion composition (2).

Example 3

100.0 parts of (A) dimethylpolysiloxane (viscosity of approximately 5,000 mPa·s), 8.3 parts of (B) aminopolyether-modified dimethylpolysiloxane (viscosity of approximately 600 mPa·s, amino group content of approximately 0.4%) represented by the following structural formula (P-2), 2.8 parts of (C-1) polyoxyethylene (4) lauryl ether (HLB=9.7), 8.0 parts of (C-2) polyoxyethylene (23) lauryl ether (HLB=16.9), 2.5 parts of (D) propylene glycol (PG), and 44.7 parts of (E) purified water were weighed into a container and were stirred•mixed to uniformity. This was followed by emulsification of the resulting mixture using a colloid mill and the addition of 0.3 part of 80% acetic acid to yield emulsion composition (3).

structural formula:

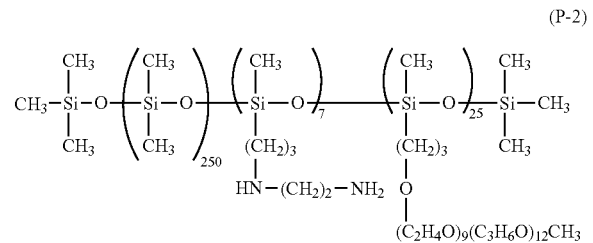

(P-2)

Example 4

100.0 parts of (A) dimethylpolysiloxane (viscosity of approximately 5,000 mPa·s), 8.3 parts of (B) amidopolyether-modified dimethylpolysiloxane (viscosity of approximately 1,000 mPa·s, amino group content of approximately 0.32%) represented by the following structural formula (P-3), 2.8 parts of (C-1) polyoxyethylene (4) lauryl ether (HLB=9.7), 8.0 parts of (C-2) polyoxyethylene (23) lauryl ether (HLB=16.9), 2.5 parts of (D) propylene glycol (PG), and 45.0 parts of (E) purified water were weighed into a container and were stirred•mixed to uniformity. This was followed by emulsification of the resulting mixture using a colloid mill to yield emulsion composition (4).

structural formula:

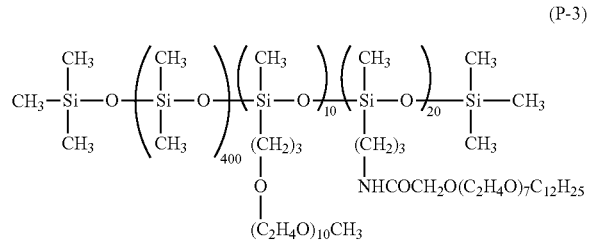

(P-3)

Example 5

100.0 parts of (A) dimethylpolysiloxane (viscosity of approximately 5,000 mPa·s), 8.3 parts of (B) epoxypolyether-modified dimethylpolysiloxane (viscosity of approximately 3,500 mPa·s, epoxy group content of approximately 0.4%) represented by the following structural formula (P-4), 2.8 parts of (C-1) polyoxyethylene (4) lauryl ether (HLB=9.7), 8.0 parts of (C-2) polyoxyethylene (23) lauryl ether (HLB=16.9), 2.5 parts of (D) propylene glycol (PG), and 45.0 parts of (E) purified water were weighed into a container and were stirred•mixed to uniformity. This was followed by emulsification of the resulting mixture using a colloid mill to yield emulsion composition (5).

structural formula:

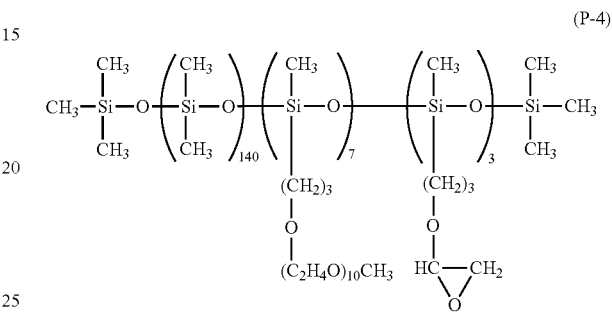

(P-4)

Example 6

100.0 parts of a mixture of (A1) dimethylpolysiloxane (viscosity of approximately 2,000,000 mPa·s) and (A2) decamethylcyclopentasiloxane (mixing ratio between (A1) and (A2)=15:85, viscosity after mixing=approximately 1,500 mPa·s), 8.3 parts of (B) amino-modified dimethylpolysiloxane (viscosity of approximately 1,200 mPa·s, amino=approximately 0.9%) represented by the preceding structural formula (P-1), 2.8 parts of (C-1) polyoxyethylene (4) lauryl ether (HLB=9.7), 8.0 parts of (C-2) polyoxyethylene (23) lauryl ether (HLB=16.9), 2.5 parts of (D) propylene glycol (PG), and 44.7 parts of (E) purified water were weighed into a container and were stirred•mixed to uniformity. This was followed by emulsification of the resulting mixture using a colloid mill and the addition of 0.3 part 80% acetic acid to yield emulsion composition (6).

Comparative Example 1

108.3 parts of (A) dimethylpolysiloxane (viscosity of approximately 5,000 mPa·s), 2.8 parts of (C-1) polyoxyethylene (4) lauryl ether (HLB=9.7), 8.0 parts of (C-2) polyoxyethylene (23) lauryl ether (HLB=16.9), and 47.5 parts of (E) purified water were weighed into a container and were stirred•mixed to uniformity. This was followed by emulsification of the resulting mixture using a colloid mill to yield emulsion composition (7).

Comparative Example 2

108.3 parts of (A) dimethylpolysiloxane (viscosity of approximately 5,000 mPa·s), 2.8 parts of (C-1) polyoxyethylene (4) lauryl ether (HLB=9.7), 8.0 parts of (C-2) polyoxyethylene (23) lauryl ether (HLB=16.9), 2.5 parts of (D) propylene glycol (PG), and 47.5 parts of (E) purified water were weighed into a container and were stirred•mixed to uniformity. This was followed by emulsification of the resulting mixture using a colloid mill to yield emulsion composition (8).

Comparative Example 3

100.0 parts of a mixture of (A1) dimethylpolysiloxane (viscosity of approximately 2,000,000 mPa·s) and (A2) decamethylcyclopentasiloxane (mixing ratio between (A1) and (A2)=15:85, viscosity after mixing=approximately 1,500 mPa·s), 8.3 parts of (B) amino-modified dimethylsiloxane (viscosity of approximately 1,200 mPa·s, amino=approximately 0.9%), 2.8 parts of (C-1) polyoxyethylene (4) lauryl ether (HLB=9.7), 8.0 parts of (C-2) polyoxyethylene (23) lauryl ether (HLB=16.9), and 47.2 parts of (E) purified water were weighed into a container and were stirred•mixed to uniformity. This was followed by emulsification of the resulting mixture using a colloid mill and the addition of 0.3 part 80% acetic acid to yield emulsion composition (9).

The results for the average emulsion particle size (μm) and the storage stability (weeks) for each of the emulsion compositions (1) to (9) in Example 1 to Comparative Example 3 were shown in below Table 1. While the average emulsion particle sizes in the examples were about the same as in the comparative examples, the storage stability of the emulsion compositions according to the examples was significantly better than for the emulsion compositions of the comparative examples.

purified water were weighed into a container and were stirred•mixed to uniformity. This was followed by emulsification of the resulting mixture using a colloid mill to yield emulsion composition (10). This composition and its average emulsion particle size (μm) are shown in Table 2.

Production Example 2

100.0 parts of (A) dimethylpolysiloxane (viscosity of approximately 5,000 mPa·s), 8.3 parts of (B) amino-modified dimethylpolysiloxane (viscosity of approximately 1,200 mPa·s, amino content of approximately 0.9%) represented by the preceding structural formula (P-1), 36.1 parts of (F) cetyltrimethylammonium chloride (30% aqueous solution), 2.5 parts of (D) propylene glycol (PG), and 19.7 parts of (E) purified water were weighed into a container and were stirred•mixed to uniformity. This was followed by emulsification of the resulting mixture using a colloid mill to yield emulsion composition (11). This composition and its average emulsion particle size (μm) are shown in Table 2.

TABLE 2

| | | (10) | (11) |
|---|---|---|---|
| emulsion composition no. | | | |
| component (A): organosiloxane | dimethylpolysiloxane (5,000 mPa·s) | 100.0 | 100.0 |
| component (B): organic-modified siloxane | amino-modified dimethylpolysiloxane | 8.3 | 8.3 |

TABLE 1

| | | examples | | | | | | comparative examples | | |
|---|---|---|---|---|---|---|---|---|---|---|
| | | 1 | 2 | 3 | 4 | 5 | 6 | 1 | 2 | 3 |
| emulsion composition no. | | (1) | (2) | (3) | (4) | (5) | (6) | (7) | (8) | (9) |
| component (A): organosiloxane | dimethylpolysiloxane (5,000 mPa·s) | 100.0 | 100.0 | 100.0 | 100.0 | 100.0 | | 108.3 | 108.3 | |
| | dimethylpolysiloxane (mixture) | | | | | | 100.0 | | | 100.0 |
| component (B): organic-modified siloxane | amino-modified | 8.3 | 8.3 | | | | 8.3 | | | 8.3 |
| | aminopolyether-modified | | | 8.3 | | | | | | |
| | amidopolyether-modified | | | | 8.3 | | | | | |
| | epoxypolyether-modified | | | | | 8.3 | | | | |
| component (C): nonionic surfactant | POE(4) lauryl ether | 2.8 | 2.8 | 2.8 | 2.8 | 2.8 | 2.8 | 2.8 | 2.8 | 2.8 |
| | POE(23) lauryl ether | 8.0 | 8.0 | 8.0 | 8.0 | 8.0 | 8.0 | 8.0 | 8.0 | 8.0 |
| component (D): water-soluble solvent | ethanol | 2.5 | | | | | | | | |
| | glycerol | | 2.5 | | | | | | | |
| | propylene glycol | | | 2.5 | 2.5 | 2.5 | 2.5 | | 2.5 | |
| component (E): purified water | | 44.7 | 44.7 | 44.7 | 45.0 | 45.0 | 44.7 | 47.5 | 45.0 | 47.2 |
| 80% acetic acid | | 0.3 | 0.3 | 0.3 | | | 0.3 | | | 0.3 |
| particle size (μm) | | 2.4 | 2.2 | 3.1 | 4.4 | 4.9 | 3.0 | 3.8 | 3.2 | 2.4 |
| storage stability (weeks) | | 20 | 20 | 16 | 16 | 16 | 20 | 4 | 4 | 6 |

Production Example 1

100.0 parts of (A) dimethylpolysiloxane (viscosity of approximately 5,000 mPa·s), 8.3 parts of (B) amino-modified dimethylpolysiloxane (viscosity of approximately 1,200 mPa·s, amino=approximately 0.9%) represented by the preceding structural formula (P-1), 43.3 parts of (F) sodium polyoxyethylene (3) lauryl sulfate (25% aqueous solution), 2.5 parts of (D) propylene glycol (PG), and 12.5 parts of (E)

TABLE 2-continued

| | | (10) | (11) |
|---|---|---|---|
| emulsion composition no. | | | |
| component (F): ionic surfactant | sodium POE(3) lauryl sulfate (25% aqueous solution) | 43.3 | |
| | cetyltrimethylammonium chloride (30% aqueous solution) | | 36.1 |

TABLE 2-continued

| emulsion composition no. | (10) | (11) |
|---|---|---|
| component (D): propylene glycol water-soluble solvent | 2.5 | 2.5 |
| component (E): purified water | 12.5 | 19.7 |
| particle size (μm) | 2.5 | 2.4 |

Production Example 3

Production of a Cationic Cosmetic Base 7.1 parts of stearyltrimethylammonium chloride (28% aqueous solution), 2.0 parts of cetostearyl alcohol, and 90.9 parts of ion-exchanged water were weighed into a container and were heated while stirring until a liquid temperature of approximately 80° C. was reached. This was followed by gradual cooling to room temperature while continuing to stir, thus yielding a cationic cosmetic base.

Production Example 4

Production of an Anionic Cosmetic Base 40.0 parts of sodium polyoxyethylene (3) lauryl sulfate (25% aqueous solution) and 60.0 parts of ion-exchanged water were weighed into a container and were thoroughly mixed at room temperature until uniformity was achieved to produce an anionic cosmetic base.

Example 7

97.0 parts of the cationic cosmetic base prepared in Production Example 3 and 3.0 parts of the emulsion composition (2) prepared in Example 2 were weighed into a container and were mixed until uniformity was achieved. When the separation status was then checked after standing at quiescence for 1 day, the cationic cosmetic base/emulsion composition blend was uniform.

Comparative Example 4

Emulsion composition (10) was used in place of emulsion composition (2) in Example 7 and the post-mixing separation status was monitored. In this case, oil separation occurred from the cationic cosmetic base/emulsion composition (10) blend.

Example 8

97.0 parts of the anionic cosmetic base prepared in Production Example 4 and 3.0 parts of the emulsion composition (2) prepared in Example 2 were weighed into a container and were mixed until uniformity was achieved. When the separation status was then checked after standing at quiescence for 1 day, the cationic cosmetic base/emulsion composition blend was uniform.

Comparative Example 5

Emulsion composition (11) was used in place of emulsion composition (2) in Example 8 and the post-mixing separation status was monitored. In this case, a cream-like aggregate was produced from the anionic cosmetic base/emulsion composition (11) blend.

The results obtained in the preceding Examples 7 and 8 and Comparative Examples 4 and 5 are shown in Table 3. The emulsion composition (2) according to the present invention could be stably blended even into an ionic cosmetic base, i.e., a cationic cosmetic base or an anionic cosmetic base without distinction therebetween, and maintained a uniform dispersion.

TABLE 3

| | | examples | | comparative examples | |
|---|---|---|---|---|---|
| | | 7 | 8 | 4 | 5 |
| base | cationic base | 97.0 | | 97.0 | |
| | anionic base | | 97.0 | | 97.0 |
| emulsion composition | emulsion composition (2) (nonionic) | 3.0 | 3.0 | | |
| | emulsion composition (10) (anionic) | | | 3.0 | |
| | emulsion composition (11) (cationic) | | | | 3.0 |
| separation status after mixing/standing | | uniform | uniform | oil separation occurred | cream was produced |

INDUSTRIAL APPLICABILITY

The oil-in-water organopolysiloxane emulsion composition of the present invention enables organopolysiloxane emulsion particles to be blended in a stable manner into products comprising an ionic base, for example, an ionic surfactant, an ionic polymer, and so forth, and as a consequence of this advantage is useful as an additive for, for example, cosmetics, healthcare products, release agents, water repellents, fiber-treatment agents, and surface-treatment agents, in their various forms (e.g., liquid, paste, emulsion, dispersion, gel, and so forth), and is also itself useful as a release agent, water repellent, fiber-treatment agent, surface-treatment agent, coating agent, or binder for organic fiber fabrics and glass cloth. The oil-in-water organosiloxane emulsion composition of the present invention is in particular very useful as an additive for ionic cosmetics that contain, for example, an anionic compound such as a sodium polyoxyethylene alkyl sulfate or a cationic compound such as a quaternary ammonium salt type compound, and in particular is very useful as an additive for hair cosmetics and hair cleansers. The method of producing a hair cosmetic, which is characterized by the use of the aforementioned oil-in-water organosiloxane emulsion composition, is a very useful method for producing hair cosmetics that exhibit an excellent conditioning effect.

The invention claimed is:
1. An oil-in-water organopolysiloxane emulsion composition that characteristically comprises
   (A) 100 weight parts of organopolysiloxane or organopolysiloxane mixture that is represented by the general formula $R_aSiO_{(4-a)/2}$, wherein each R is independently the hydroxyl group or C1-20 monovalent hydrocarbyl that is unsubstituted or that has a portion of its hydrogen atoms replaced by halogen, and $1.8 \leq a \leq 2.2$,
   (B) 0.5 to 35 weight parts of organosiloxane that has a viscosity at 25° C. of 10 to 100,000 mPa·s and that characteristically contains in the molecule at least one type of organic group selected from the group consisting of nitrogen atom-containing organic groups and epoxy-functional organic groups, (C) 0.5 to 35 weight parts of nonionic surfactant selected from the group consisting of ethylene glycol/aliphatic acid esters, polyethylene glycol/aliphatic acid esters, propylene glycol/aliphatic acid esters, polypropylene glycol/aliphatic acid esters, glycol/aliphatic acid esters, trimethylolpropane/aliphatic acid esters, pentaerythritol/aliphatic acid esters, glucoside derivatives, aliphatic acid esters of glycerol alkyl ethers, trimethylolpropaneoxyethylene alkyl ethers, lanolin and its derivatives, caster oil derivatives, hardened caster oil derivatives, sterols and its derivatives, polyoxyethylene alkyl ethers, polyoxyethylene alkylaryl ethers, polyoxyethylene trimethylolpropane/aliphatic acid esters, polyoxyethylene alkyl ether/aliphatic acid esters, polyoxyethylene-polyoxypropylene glycols, polyoxyethylene-polyoxypropylene alkyl ethers, polyoxyethylene-polyoxypropylene polyhydric alcohol ethers, glycerol/aliphatic acid esters, polyglycerol/aliphatic acid esters, polyoxyethylene glycerol/aliphatic acid esters, sorbitan/aliphatic acid esters, polyoxyethylene sorbitan/aliphatic acid esters, and sucrose/aliphatic acid esters, (D) 0.5 to 15 weight parts of water-soluble solvent, and (E) 10 to 150 weight parts of water, wherein the content of (F) ionic surfactant in the composition is less than 0.1 weight part per 100 weight parts component (A).

2. The oil-in-water organopolysiloxane emulsion composition according to claim 1, wherein component (B) is organosiloxane that has in its molecule at least one type of monovalent organic group represented by the following structural formulas (1) to (5)

structural formula (1):

$$-R^1-N{\overset{R^2}{\underset{R^2}{\diagup}}}\phantom{}\qquad(1)$$

structural formula (2):

$$-R^1-NH-R^3-N{\overset{R^2}{\underset{R^2}{\diagup}}}\phantom{}\qquad(2)$$

structural formula (3):

$$-R^1-\overset{H}{\underset{}{C}}-\overset{H}{\underset{}{C}}-R^2 \qquad(3)$$
$$\phantom{-R^1-}\diagdown O \diagup$$

structural formula (4):

$$-R^1-\text{(cyclohexane with R}^2\text{ substituents and O)} \qquad(4)$$

structural formula (5):

$$-R^1-\underset{R^2}{\underset{|}{N}}-\underset{O}{\overset{||}{C}}-R^4 \qquad(5)$$

in structural formulas (1) to (5), each $R^1$ is independently C1-20 divalent hydrocarbyl that is unsubstituted or that has a portion of its hydrogen atoms replaced by halogen, each $R^2$ is independently a monovalent functional group selected from the group consisting of the hydrogen atom, carbinol group, and C1-20 monovalent hydrocarbyl that is unsubstituted or that has a portion of its hydrogen atoms replaced by halogen, $R^3$ is C1-10 divalent hydrocarbyl that is unsubstituted or that has a portion of its hydrogen atoms replaced by halogen, and $R^4$ is a monovalent functional group selected from the group consisting of the hydrogen atom, carbinol group, polyoxyalkylene group, and C1-50 monovalent hydrocarbyl that is unsubstituted or that has a portion of its hydrogen atoms replaced by halogen, or is a divalent organic group that is bonded to another hydrocarbon-type compound or to organosiloxane.

3. The oil-in-water organopolysiloxane emulsion composition according to claim 2, wherein component (B) is organosiloxane that additionally contains in its molecule the straight-chain or branched-chain alkylene represented by structural formula (6) below or the oxyalkylene represented by structural formula (7), wherein
structural formula (6) is:

$$-C_qH_{2q}- \qquad(6)$$

q in formula (6) is a number from 2 to 20, and structural formula (7) is:

$$-CH_2-CHR^5-O- \qquad(7)$$

$R^5$ in formula (7) is the hydrogen atom or C1-20 monovalent hydrocarbyl that is unsubstituted or that has a portion of its hydrogen atoms replaced by halogen.

4. The oil-in-water organopolysiloxane emulsion composition according to claim 1, wherein component (D) is an alcohol.

5. The oil-in-water organopolysiloxane emulsion composition according to claim 1, wherein the average particle size of the emulsion particles is in the range from 1 to 100 μm as measured by a laser diffraction•scattering procedure.

6. The oil-in-water organopolysiloxane emulsion composition according to claim 2, wherein component (A) is chain methylpolysiloxane or cyclic methylpolysiloxane having a viscosity at 25° C. of 0.65 to 30,000,000 mPa·s, or is a mixture of these methylpolysiloxanes; component (B) is the straight-chain organosiloxane represented by structural formula (8) given below; component (C) comprises nonionic surfactant; and component (D) is an alcohol, wherein
structural formula (8) is:

$$Y-\underset{R}{\overset{R}{\underset{|}{Si}}}-O{\left(\underset{R}{\overset{R}{\underset{|}{Si}}}-O\right)}_n{\left(\underset{R^a}{\overset{R}{\underset{|}{Si}}}-O\right)}_m{\left(\underset{R^b}{\overset{R}{\underset{|}{Si}}}-O\right)}_p{\left(\underset{R^c}{\overset{R}{\underset{|}{Si}}}-O\right)}_s{\left[X\right]}_r\underset{R}{\overset{R}{\underset{|}{Si}}}-Y \qquad(8)$$

in formula (8), each R is independently C1-20 monovalent hydrocarbyl that is unsubstituted or that has a portion of its hydrogen atoms replaced by halogen; each $R^a$ is a monovalent organic group independently selected from the group consisting of the monovalent organic groups represented by the preceding structural formulas (1) to (5); $R^b$ is a monovalent functional group selected from the group consisting of the hydroxyl group, carbinol, mercapto, and carboxyl; $R^c$ is a straight-chain or branched-chain alkyl as represented by the following structural formula (6') or is a polyoxyalkylene group as represented by the following structural formula (7'); X is a straight-chain or branched-chain alkylene group as represented by the preceding structural formula (6) or an oxyalkylene group as represented by the preceding structural formula (7); each Y is a group independently selected from R, $R^a$, $R^b$, and $R^c$; (n+m+p+r+s) is a number that provides a viscosity for the organopolysiloxane at 25° C. of 10 to 100,000 mPa·s; and n, m, p, r, and s are each independently 0 or a positive number, wherein when m=0, a single Y is an organic group represented by $R^a$ or both Y's are organic groups represented by $R^a$, wherein
structural formula (6') is:

q in formula (6') is a number from 2 to 20, and structural formula (7') is:

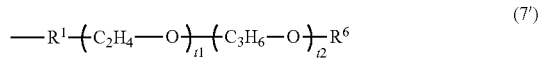

in formula (7'), $R^1$ is C1-20 divalent hydrocarbyl that is unsubstituted or that has a portion of its hydrogen atoms replaced by halogen; $R^6$ is a monovalent functional group selected from the group consisting of the hydrogen atom, carbinol, and C1-20 monovalent hydrocarbyl that is unsubstituted or that has a portion of its hydrogen atoms replaced by halogen; t1 and t2 are each 0 or a positive number; and (t1+t2) is a number in the range of 1 to 50.

7. A cosmetic ingredient comprising the oil-in-water organopolysiloxane emulsion composition according to claim 1.

8. A hair cosmetic ingredient comprising the oil-in-water organopolysiloxane emulsion composition according to claim 1.

9. A method of producing a hair cosmetic, said method comprising:
   introducing an ionic surfactant and water into a production vessel, thereafter introducing the oil-in-water organopolysiloxane emulsion composition according to claim 1 into the production vessel, and mixing with mechanical force.

10. The oil-in-water organopolysiloxane emulsion composition according to claim 2, wherein the average particle size of the emulsion particles is in the range from 1 to 100 μm as measured by a laser diffraction•scattering procedure.

11. The oil-in-water organopolysiloxane emulsion composition according to claim 3, wherein the average particle size of the emulsion particles is in the range from 1 to 100 μm as measured by a laser diffraction•scattering procedure.

12. The oil-in-water organopolysiloxane emulsion composition according to claim 1, wherein component (C) is 0.5 to 15 weight parts of nonionic surfactant selected from the group consisting of trimethylolpropaneoxyethylene alkyl ethers, polyoxyethylene alkyl ethers, polyoxyethylene alkylaryl ethers, polyoxyethylene-polyoxypropylene alkyl ethers, and polyoxyethylene-polyoxypropylene polyhydric alcohol ethers.

* * * * *